US007774063B2

(12) United States Patent
Ghanem et al.

(10) Patent No.: US 7,774,063 B2
(45) Date of Patent: Aug. 10, 2010

(54) METHOD AND APPARATUS FOR DISCRIMINATING CARDIAC SIGNALS IN A MEDICAL DEVICE BASED ON WAVELET DECOMPOSITION ANALYSIS

(75) Inventors: Raja N. Ghanem, Edina, MN (US); Troy E. Jackson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 288 days.

(21) Appl. No.: 11/744,484

(22) Filed: May 4, 2007

(65) Prior Publication Data

US 2007/0260153 A1 Nov. 8, 2007

Related U.S. Application Data

(60) Provisional application No. 60/746,561, filed on May 5, 2006.

(51) Int. Cl.
*A61N 1/37* (2006.01)
(52) U.S. Cl. .............................. 607/27; 607/2; 600/515
(58) Field of Classification Search .................. 600/453, 600/509–510, 515; 702/189; 455/313; 435/6; 607/27.5
See application file for complete search history.

(56) References Cited

U.S. PATENT DOCUMENTS

| 4,374,382 | A | 2/1983 | Markowitz |
| 5,117,824 | A | 6/1992 | Keimel et al. |
| 5,193,535 | A | 3/1993 | Bardy et al. |
| 5,545,186 | A | 8/1996 | Olson et al. |
| 6,067,473 | A | 5/2000 | Greeninger et al. |
| 6,393,316 | B1 * | 5/2002 | Gillberg et al. ............. 600/515 |
| 7,076,289 | B2 * | 7/2006 | Sarkar et al. ................ 600/515 |
| 7,167,747 | B2 * | 1/2007 | Gunderson et al. ............. 607/9 |
| 2002/0023066 | A1 * | 2/2002 | Fu et al. ....................... 706/22 |
| 2004/0127945 | A1 * | 7/2004 | Collins et al. .................. 607/5 |
| 2008/0015452 | A1 * | 1/2008 | Ricci et al. .................. 600/509 |

OTHER PUBLICATIONS

Cuiwei et al. "Detection of ECG Characteristic Points Using Wavelet Transforms"; IEEE Transactions on Biomedical Engineering; vol. 42, No. 1; Jan. 1995.*

* cited by examiner

*Primary Examiner*—Carl H Layno
*Assistant Examiner*—Paula J Stice
(74) *Attorney, Agent, or Firm*—Michael C. Soldner

(57) ABSTRACT

A method and device for detecting cardiac signals in a medical device that includes decomposing sensed cardiac signals using a wavelet function to form a corresponding wavelet transform, generating a first wavelet representation corresponding to the wavelet transform that is responsive to RR intervals of the sensed cardiac signals, generating a second wavelet representation that is not responsive to RR intervals associated with the sensed cardiac signals, determining a no lead failure zone in response to the first wavelet representation and the second wavelet representation, and distinguishing the cardiac event from a device failure in response to the determined no lead failure zone. The method and device may also include generating a wavelet representation corresponding to the wavelet transform that is not responsive to RR intervals of the sensed cardiac signals, determining RR intervals associated with the sensed cardiac signals, and determining a no lead failure zone in response to the wavelet representation and the determined RR intervals.

21 Claims, 10 Drawing Sheets

METHOD AND APPARATUS FOR DISCRIMINATING CARDIAC SIGNALS IN A MEDICAL DEVICE BASED ON WAVELET DECOMPOSITION ANALYSIS

RELATED APPLICATION

The present application claims priority and other benefits from U.S. Provisional Patent Application Ser. No. 60/746,561, filed May 5, 2006, entitled "METHOD AND APPARATUS FOR DISCRIMINATING CARDIAC SIGNALS IN A MEDICAL DEVICE BASED ON WAVELET DECOMPOSITION ANALYSIS", incorporated herein by reference in its entirety.

CROSS-REFERENCE TO RELATED APPLICATION

Cross-reference is hereby made to the commonly-assigned related U.S. Applications, Ser. No. 11/744,455, entitled "METHOD AND APPARATUS FOR DISCRIMINATING CARDIAC SIGNALS IN A MEDICAL DEVICE BASED ON WAVELET DECOMPOSITION ANALYSIS", to Ghanem et al., and 11/744,475, entitled "METHOD AND APPARATUS FOR DISCRIMINATING CARDIAC SIGNALS IN A MEDICAL DEVICE BASED ON WAVELET DECOMPOSITION ANALYSIS", to Ghanem et al., both filed concurrently herewith and incorporated herein by reference in their entireties.

FIELD OF THE INVENTION

The present invention relates generally to medical devices, and more particularly to a method and apparatus for discriminating cardiac signals based on wavelet decomposition analysis.

BACKGROUND OF THE INVENTION

Lead failure (set screws, subclavian crush, header, adapter, etc.) remain a major cause of inappropriate detection and therapy in patients receiving transvenous implantable cardioverter defibrillator (ICDs). Lead failure accounts for 54% of inappropriate detection due to oversensing. Lead failure typically exhibits as saturated or signal portions with high slew rates.

ICD's detect ventricular arrhythmia whenever a specific number of short depolarization intervals is reached. For example, 12 out of 16 intervals falling into the fibrillation detection interval (FDI) will trigger VF detection at which point charging is initiated. Upon charge completion, a shock is delivered. Lead failure due to fast transients in the signal, also exhibit as short depolarization intervals which are often inappropriately detected as VF resulting in reduced specificity.

Typically, broken electrodes, lead fractures, or signal saturations demonstrate as singularities (fast transients with very large slew rates, step-like transitions) on the recorded electrograms or electrocardiograms. These are usually closely coupled and short lived. What is needed is a method and apparatus that addresses these signal characteristics (sharp fast transitions that are closely coupled in time) during wavelet decomposition analysis in order to detect lead failure.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF THE INVENTION

Figure 1:
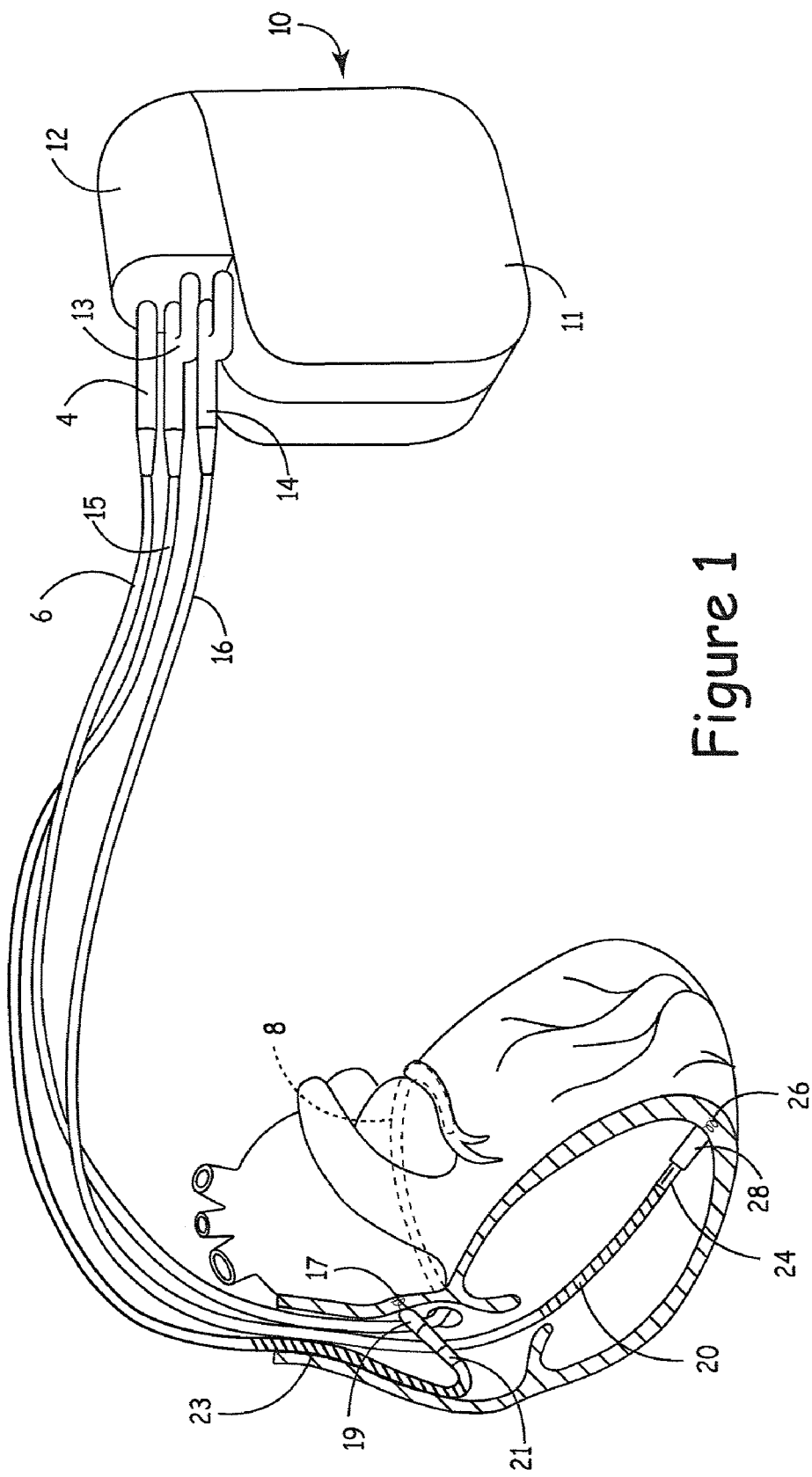
FIG. 1 is a schematic diagram of an exemplary medical device in which the present invention may be utilized.

An exemplary implantable cardioverter/defibrillator (ICD) 10 is shown in FIG. 1, with which methods included in the present invention may be used. In accordance with the invention, ICD 10 identifies oversensing and automatically provides a corrective action, e.g., adjusts one or more detection parameters to avoid future inappropriate detections. Particularly, ICD 10 operates in accordance with originally programmed sensing and detection parameters for a plurality of cardiac cycles, and upon detecting oversensing, automatically provides the corrective action to avoid possible future inappropriate detections. In this manner, the corrective actions provided by ICD 10 to avoid future inappropriate detections are dynamically performed.

The ICD 10 is shown coupled to a heart of a patient by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, non-transvenous cardiac device, or other cardiac monitoring device.

Figure 2:
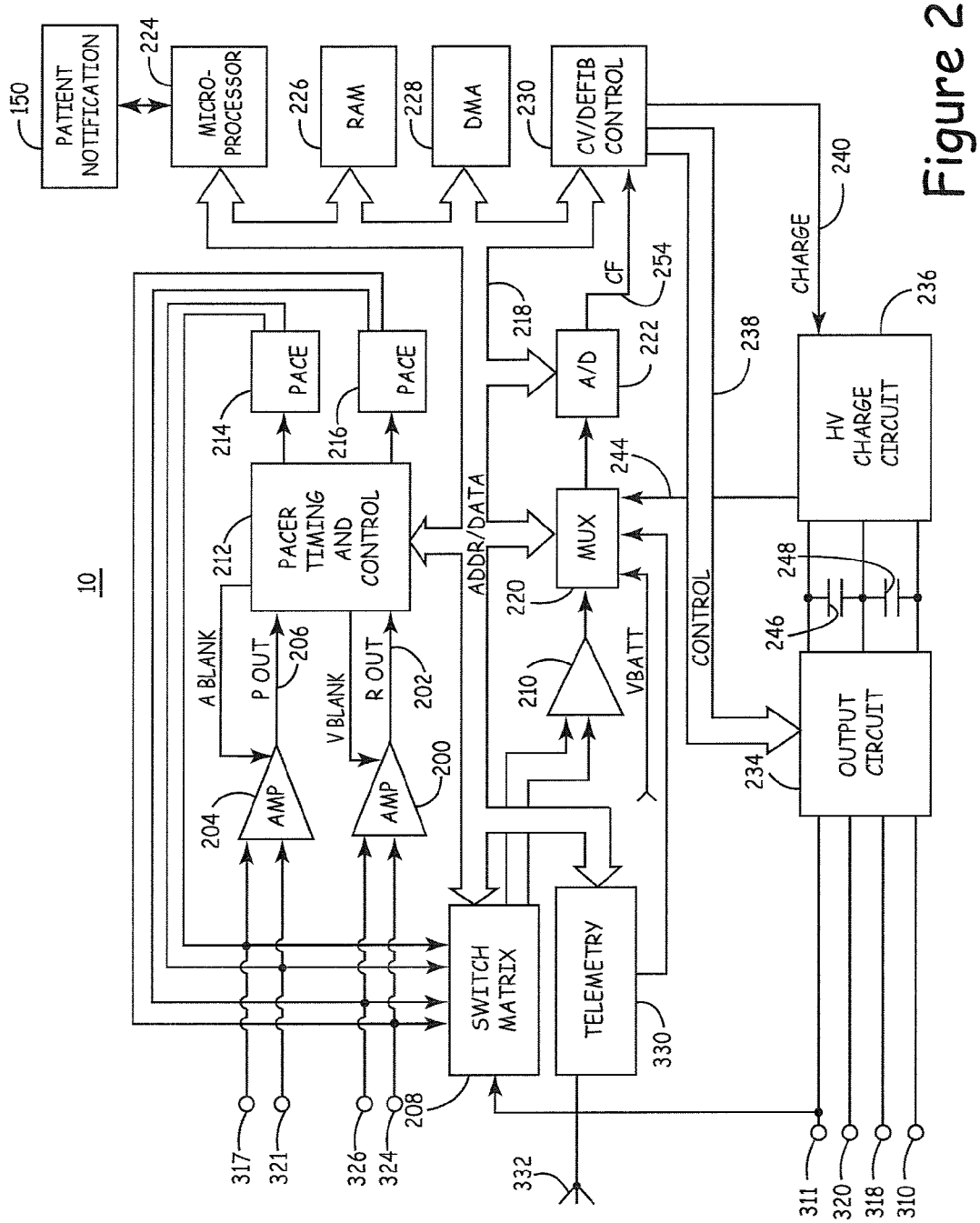
FIG. 2 is a functional schematic diagram of the device of FIG. 1.

A functional schematic diagram of the ICD 10 is shown in FIG. 2. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensitivity. Atrial sense amplifier 204 and ventricular sense amplifier 200 receive timing information from pacer timing and control circuitry 212. Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock.

The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy, incorporated herein by reference in its entirety. Annotation of sensed events, which may be displayed and stored with EGM data, is described in U.S. Pat. No. 4,374,382 issued to Markowitz, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Wavelet decomposition analysis offers the unique opportunity to analyze localized time and frequency information content in the intracardiac electrogram. Using dyadic wavelet decomposition, it is possible to characterize a signal from the wavelet transform maxima. Additionally, using wavelets with increasing number of vanishing moments, it is possible to characterize the smoothness of the input signal. The local extrema in the wavelet transform correlate with the signal transients and its derivatives. The present invention relates to evaluation of the wavelet transform computed using one or more mother wavelets, such as a Haar wavelet or a Daubechies $4^{th}$ order wavelet, for example, for the development of potential discriminators that can differentiate lead failure (or any sharp signal transients or singularities) from ventricular fibrillation (VF) by wavelet decomposition analysis.

Wavelet decomposition involves representing a given signal as a weighted superposition of linear combinations of some basis wavelets (such as Haar or Daubechies wavelets) that are dilated and scaled. The weights corresponding to these bases are determined from the inner product between the given signal and the particular scaled and dilated wavelet. The basis wavelets are functions that have a zero mean, are typically of finite support (duration) and satisfy a specific condition. The wavelets are scaled and dilated to evaluate different time and frequency content information in the signal. A short duration wavelet has good time resolution but poor frequency resolution. A long duration wavelet has poor time resolution but good frequency resolution. Using wavelet decomposition, both time and frequency content can be analyzed at different scales.

Figure 3:
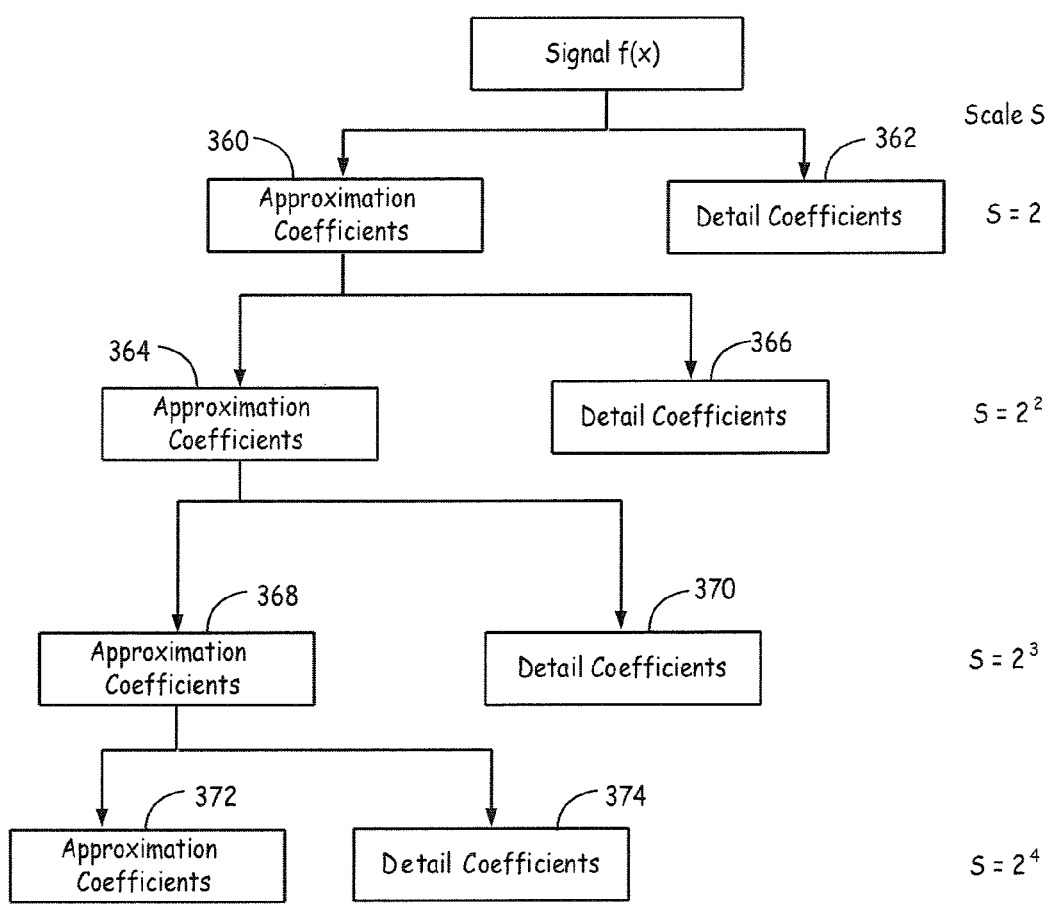
FIG. 3 is a block diagram of discrete wavelet transform decomposition utilized in a method of identifying cardiac signals according to an embodiment of the present invention.

FIG. 3 is a block diagram of discrete wavelet transform decomposition utilized in a method of identifying cardiac signals according to an embodiment of the present invention. As illustrated in FIG. 3, at each level (scale s), the signal is decomposed into a pair of approximation (lowpass frequency content) and detail (highpass frequency content) coefficients.

On a subsequent level the approximation coefficients are further decomposed into approximation and detail coefficients. This process is performed up to $2^N$th level. In the example of FIG. 3, the decomposition is performed up to 4 levels implying a scale of $2^4$ as the coarse scale. In particular, the signal f(x) is decomposed at the first level, S=2, into a first pair that includes approximation coefficients 360 and detail coefficients 362. At the next or second level, $S=2^2$, the approximation coefficients 360 from the previous level are further decomposed into a second pair that includes approximation coefficients 364 and detail coefficients 366. At the next or third level, $S=2^3$, the approximation coefficients 364 from the previous level are further decomposed into a second pair that includes approximation coefficients 368 and detail coefficients 370. At the next or fourth level, $S=2^4$, the approximation coefficients 368 from the previous level are further decomposed into a second pair that includes approximation coefficients 372 and detail coefficients 374. In this way, the input signal f(x) is therefore completely described by approximation coefficients 372, approximation coefficients 368, approximation coefficients 364, approximation coefficients 360, detail coefficients 374, detail coefficients 370, detail coefficients 366 and detail coefficients 362 by summation of the sequences generated from the inner product of each set of these coefficients with the input signal f(x).

By studying the detail and approximation coefficients it is possible to analyze signal characteristics during signal singularities/transients/or sharp transitions. The present invention utilizes the approximate coefficients at the coarse scale (approximation coefficients 372) to provide an estimate of the variation of transients in the signal and the detail coefficients at the finest scale (detail coefficients 362) to provide a rate estimate.

By applying the Haar wavelet and computing the detail (highpass) and approximation (lowpass) representations (herein referred to as detail sequences and approximation sequences), statistical measures are then computed in order to discriminate signal singularities from VF. At fine scales, the detail sequences represent the ventricular depolarizations (R-waves). At coarse scales, the wavelet transform approximations represent the DC shift or average value of the signal.

Current known lead failure algorithms have incorporated lead impedance measurements (as a surrogate to lead quality: high values signify open circuit or broken lead) and number of short RR interval counts (RR is defined as the time interval between consecutive depolarization, i.e. R-waves). However, it is not possible to measure electrode impedance when pacing circuitry is not available. More recent algorithms rely on measurements made on the far field electrogram when the sensed rate from the near field electrogram falls in the VTNF shock zone. In the present invention, a potential approach for lead failure detection utilizes the near field electrogram without relying on far field electrogram measurements. The potential for this approach lies in the possibility to detect electrode failure when impedance measurements through the electrode to assess tissue/electrode/lead functionality are not possible. In addition, this approach could be used to detect sudden transients in the ECG or electrogram and therefore preclude the need for blanking post pace or post shock. Today's ICDs blank the sensing amplifier hardware post pacing or post shock in order not to sense the recovery from polarization which often exhibits as sharp and fast transients. Using the technique presented by the present invention, polarization, like singularities, can be detected and detection can be withheld accordingly without the need to blank the sensing amplifiers.

In order to detect short durations of signal discontinuities, it is essential to choose a wavelet function such that the length of the lowpass and highpass wavelet decomposition filters is short. These filters are utilized to compute the approximation sequences and the detail sequences. The use of the wavelet transform in accordance with the invention adds value in representing a signal that is a mix of sharp transients and slowly varying components as is the case with lead failure, saturated signals, or signals recovering post shock due to electrode polarization. According to the present invention, it is feasible to use wavelet decomposition to characterize lead failure (or more generally singularities in the signal) and to potentially discriminate that from ventricular fibrillation.

In a method of identifying cardiac signals according to an embodiment of the present invention, a cardiac signal is decomposed using a first wavelet function at a first plurality of scales to form a corresponding wavelet transform. First approximation and detail sequences are determined in response to the first plurality of scales.

In another embodiment of the present invention, a cardiac signal is decomposed using a first wavelet function at a first plurality of scales to form a corresponding wavelet transform, and first approximation sequences are determined in response to the first plurality of scales. A comparison of dispersion associated with the determined first approximation sequences is then made.

According to another embodiment of the present invention, a wavelet representation of the wavelet transform is reconstructed using predetermined approximation coefficients of the determined first approximation coefficients, wherein the comparing is in response to the reconstructed wavelet representation. In another embodiment, the cardiac signal is decomposed using a second wavelet function at a second plurality of scales to form a corresponding second wavelet transform, second approximation sequences are determined in response to the second plurality of scales, and dispersion associated with the determined second approximation sequences is compared.

According to an embodiment of the present invention, a wavelet representation of the second wavelet transform is constructed using predetermined approximation coefficients of the determined second approximation coefficients, wherein the comparing dispersion associated with the determined second approximation coefficients is in response to the reconstructed wavelet representation of the second wavelet transform. The compared dispersion associated with the reconstructed wavelet representation of the first wavelet transform and the reconstructed wavelet representation of the second wavelet transform is then analyzed.

According to the present invention the cardiac signal is identified as being associated with ventricular fibrillation in response to the compared dispersion being less than a dispersion threshold, and the cardiac signal is identified as being associated with a corruption of a lead in response to the compared dispersion not being less than the dispersion threshold.

It is understood that, according to the present invention, the first approximation coefficients may be either the same or different than the second approximation coefficients.

Figure 4:
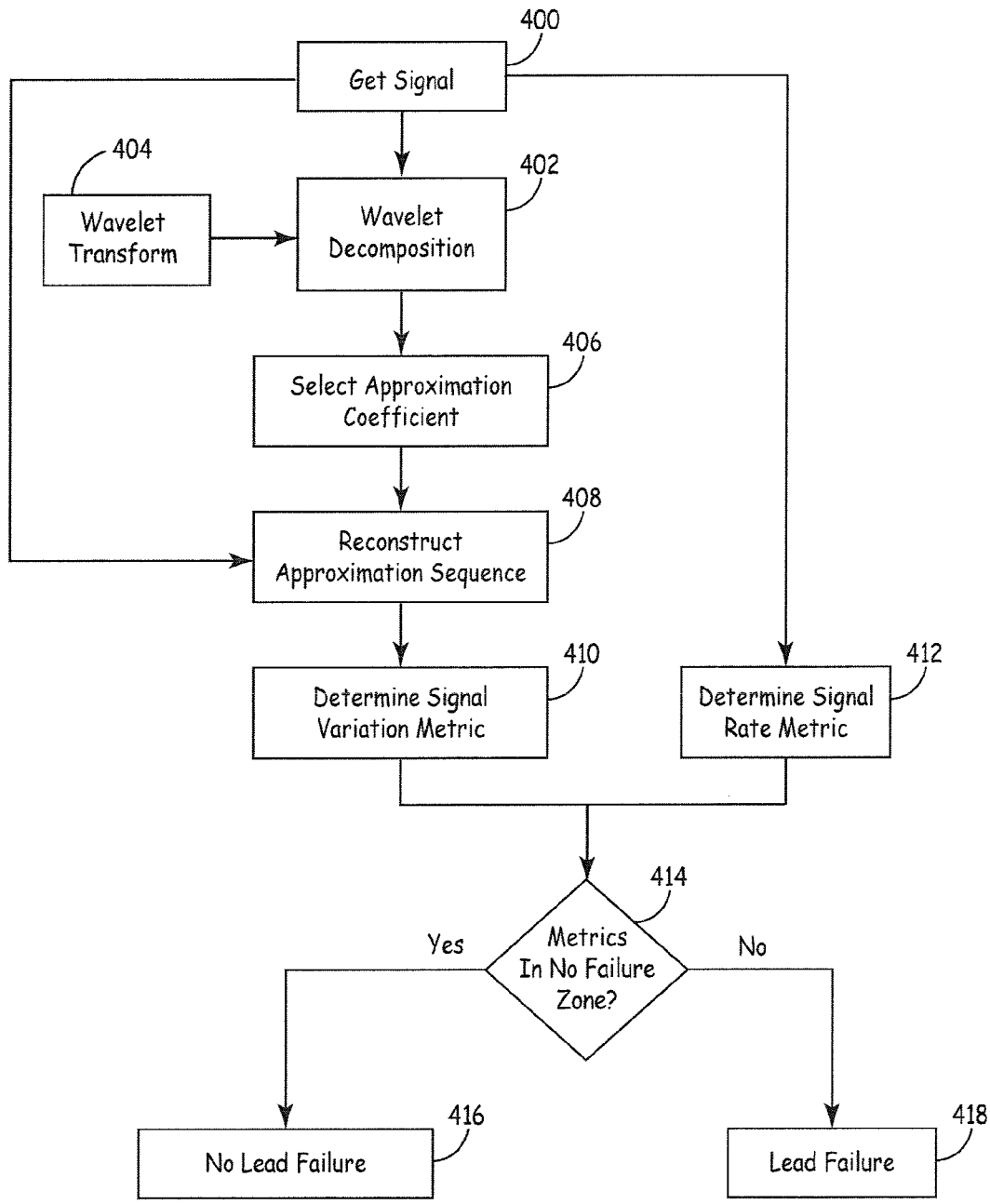
FIG. 4 is a flowchart of a method for detecting lead failure according to an embodiment of the present invention.

FIG. 4 is a flowchart of a method for detecting lead failure according to an embodiment of the present invention. As illustrated in FIG. 4, according to an embodiment of the invention, an EGM signal associated with cardiac signals sensed by the device is acquired, Block 400, so that a wavelet decomposition is performed, Block 402, on the obtained signal using a wavelet transform, Block 404, such as a Haar wavelet for example. According to an embodiment of the invention, the wavelet decomposition utilized in Block 402 is performed to 4 levels, implying a scale of $2^4$ as the course scale. Once the wavelet decomposition has been performed, the device selects the approximation coefficients, Block 406, previously obtained from the determined wavelet decomposition of Block 402. For example, according to an embodiment of the present invention, the device selects the approximation coefficients at the most course scale, i.e., $S=2^4$, as the signal variation characteristic.

The approximation sequence, or signal is then re-constructed, Block 408, using the initially detected EGM signal, Block 400, obtained prior to the wavelet decomposition, Block 402, and the selected approximation coefficients, Block 406. Once the approximation sequence has been reconstructed in Block 408, the device determines a signal variation metric, Block 410, described below, based on the reconstructed approximation sequence, Block 408. In addition to determining a signal variation metric, Block 410, the device also determines a signal rate metric, Block 412, based on the initially detected EGM signal obtained in Block 400. The device then determines whether both the signal variation metric and the signal rate metric are within a no lead failure zone, Block 414, described below. If both the signal variation metric and the signal rate metric are within the no lead failure zone, Yes in Block 414, a lead failure is not detected, Block 416, and the detection and therapy delivery process resumes as normal. If one or both of the signal variation metric and the signal rate metric are outside the no lead failure zone, No in Block 414, a lead failure is detected, Block 418, and VTNF detection is withheld, thereby enhancing specificity. Additionally, repeated lead failure detections may trigger a patient alert.

According to the present invention, the signal variation metric and the signal rate metric are chosen in such a way as to maximize both the sensitivity and the specificity of the device in identifying a lead failure. For example, the inventors have discovered that both specificity and sensitivity are maximized by using the combination of a mean rectified amplitude MRA associated with the reconstructed signal of Block 408 as the signal variation metric, and a mean absolute difference $MAD_{rr}$ between RR intervals associated with the initially detected EGM signal obtained in Block 400 as the signal rate metric.

Therefore, during the determination of the signal variation metric of Block 410, the device generates sample amplitudes of the reconstructed signal of Block 408 over a predetermined window, such as a three second window for example, so that if the device generates the amplitude samples at a rate of 256 samples per second, the sampling results in 768 total amplitude samples being generated. The device then determines the mean rectified amplitude MRA associated with the three second window by dividing the sum of the absolute values of each of the amplitude samples by the total number of sample, and sets the signal variation metric, Block 410, equal to the determined mean rectified amplitude. Similarly, in order to determine the signal rate metric of Block 412, the device first determines an overall mean of a predetermined number of RR intervals from the initially detected EGM signal, Block 400, determines the mean absolute difference $MAD_{rr}$ between the RR intervals by dividing the sum of the absolute difference between each RR interval and the predetermined overall mean by the total number of samples, and sets the signal rate metric equal to the determined mean absolute difference $MAD_{rr}$.

According to another embodiment of the invention, the signal rate metric is determined based on the determined mean absolute difference $MAD_{rr}$, as described above. However, rather than utilizing the mean rectified amplitude MRA for the signal variation metric, the device determines an amplitude dispersion $DISP_A$ of the sample amplitudes for the three second window of the reconstructed approximation sequence by determining a difference between a maximum amplitude of the sample amplitudes and a minimum amplitude of the samples amplitudes, and sets the signal variation metric equal to the determined amplitude dispersion $DISP_A$. Therefore, both specificity and sensitivity are maximized by using the combination of an amplitude dispersion $DISP_A$ associated with the reconstructed signal of Block 408 as the signal variation metric, and a mean absolute difference $MAD_{rr}$ between RR intervals associated with the initially detected EGM signal obtained in Block 400 as the signal rate metric.

Figure 5:
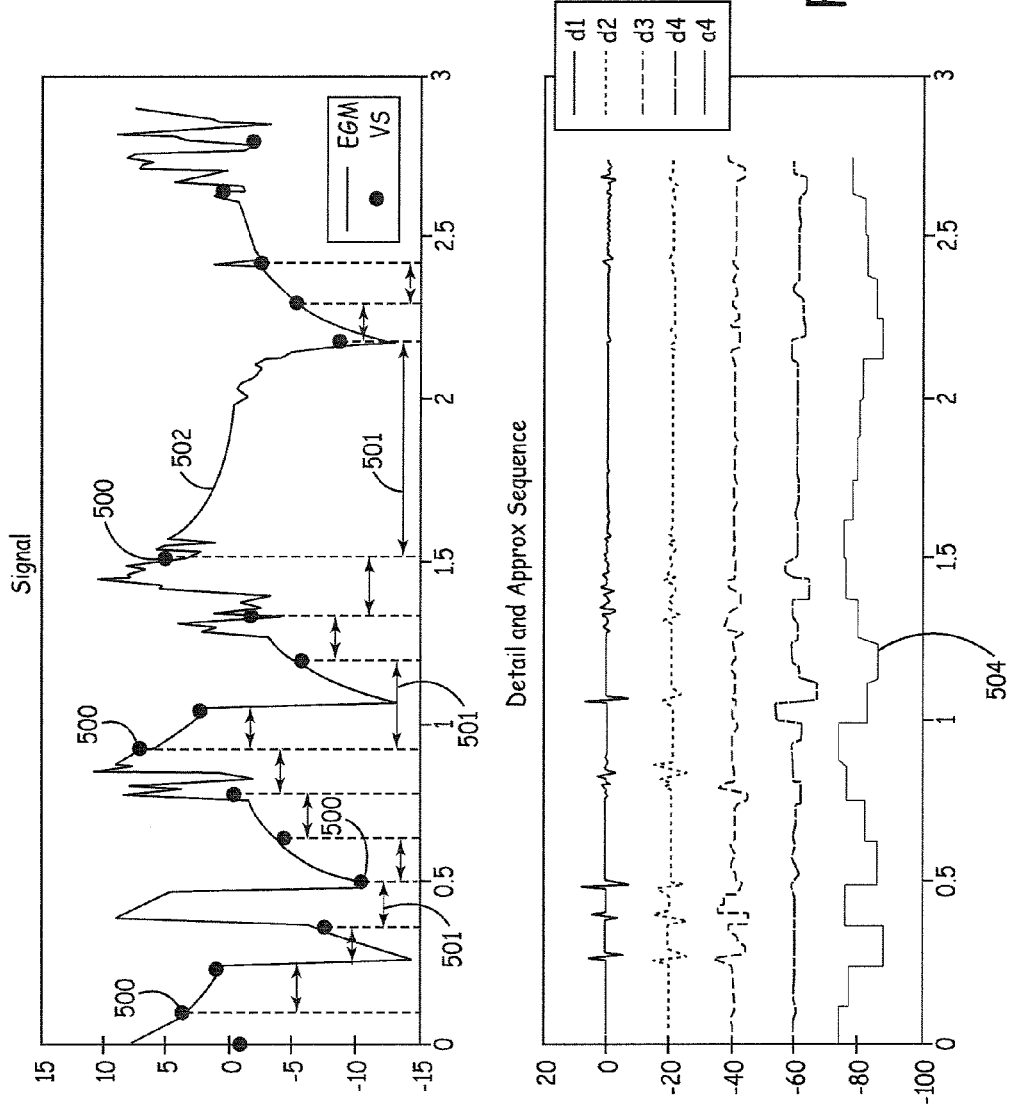
FIGS. 5-7 are graphical representations of detection of a lead failure according to an embodiment of the present invention.
Figure 6:
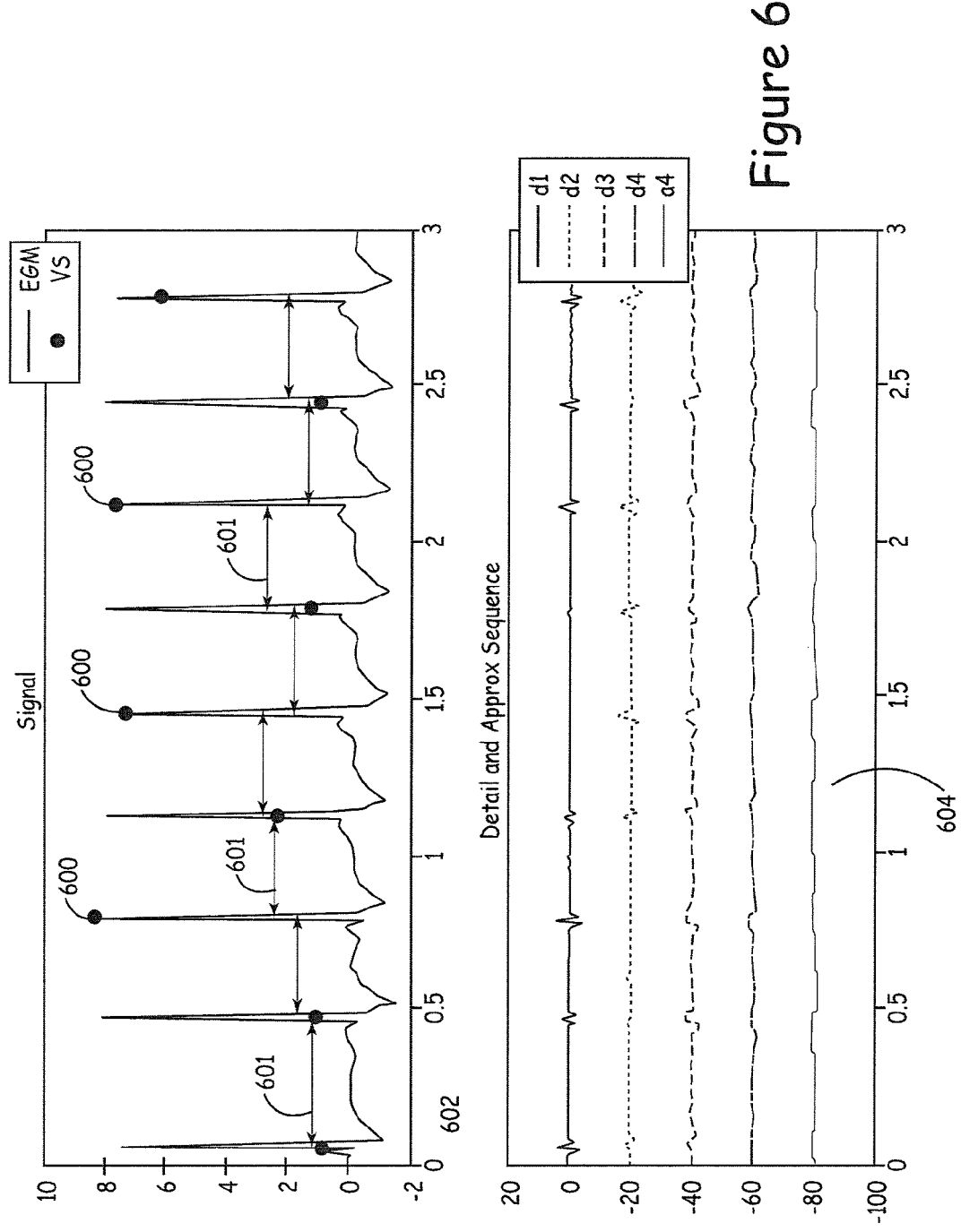
Figure 7:
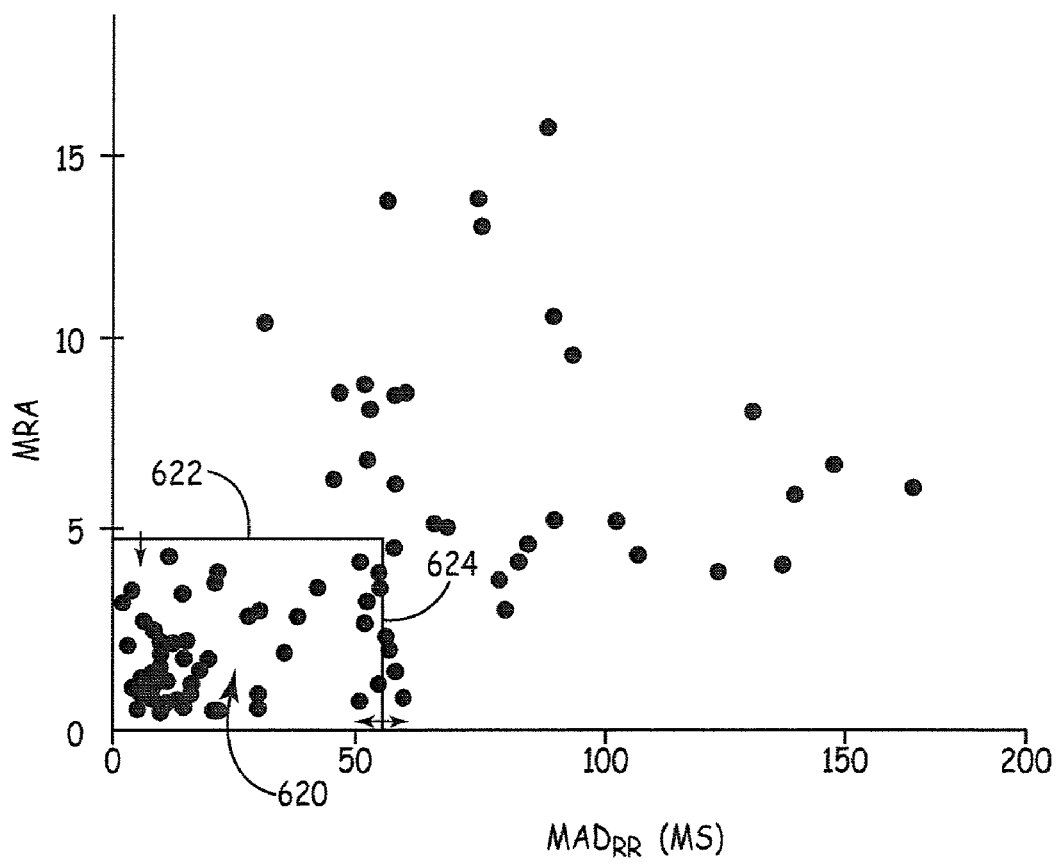

FIGS. 5-7 are graphical representations of detection of a lead failure according to an embodiment of the present invention. FIGS. 5 and 6 are exemplary illustrations of an appropriately detected lead failure and VF event. As illustrated in FIGS. 5 and 6, it can be deduced that the mean absolute difference between RR-intervals 501 associated with adjacent v-senses 500 of an initially detected EGM signal 502 during a lead failure is greater than the mean absolute difference between RR-intervals 601 associated with adjacent v-senses 600 of an initially detected EGM signal 602 when there is no lead failure. In addition, both a mean rectified amplitude associated with an approximation sequence at the most course scale 504 during lead failure is greater compared to the mean rectified amplitude of an approximation sequence at the most course scale 604 when there is VF with no lead failure, and the amplitude dispersion associated with an approximation sequence at the most course scale 504 during lead failure is greater compared to the amplitude dispersion associated with an approximation sequence at the most course scale 604 when there is VF with no lead failure.

Therefore, as illustrated in FIG. 7, according to an embodiment of the present invention, a no lead failure zone 620 is defined based on the relationship between a predetermined mean rectified amplitude MRA threshold associated with the reconstructed signal of Block 408 and a mean absolute difference $MAD_{rr}$ threshold associated with RR intervals of the initially detected EGM signal. For example, the no lead failure zone 620 is defined by a first boundary 622 associated with the MRA threshold and a second boundary 624 associated with the $MAD_{rr}$ threshold. According to an embodiment of the present invention, illustrated in FIG. 7 for example, the MRA amplitude threshold is set as 4.7 and the $MAD_{rr}$ threshold is set as 52.5 ms. According to another embodiment, a no lead failure zone 620 is defined based on the relationship between a predetermined amplitude dispersion $DISP_A$ threshold associated with the reconstructed signal of Block 408 and a mean absolute difference $MAD_{rr}$ threshold associated with RR intervals of the initially detected EGM signal. In particular, for example, the no lead failure zone 620 is defined by a first boundary 622 associated with the amplitude dispersion $DISP_A$ threshold and a second boundary 624 associated with the mean absolute difference $MAD_{rr}$ threshold. According to an embodiment of the present invention, the dispersion $DISP_A$ threshold is set as 7 and the $MAD_{rr}$ threshold is set as 70 ms.

In this way, the signal variation metric and the signal rate metric are determined to be within the no lead failure zone 620 and therefore lead failure is not detected if both the mean rectified amplitude is less than the first boundary 622, i.e., the MRA threshold in one embodiment or the dispersion $DISP_A$ threshold in another embodiment, and the mean of the absolute differences is less than the second boundary, i.e., the $MAD_{rr}$ threshold.

Figure 8:
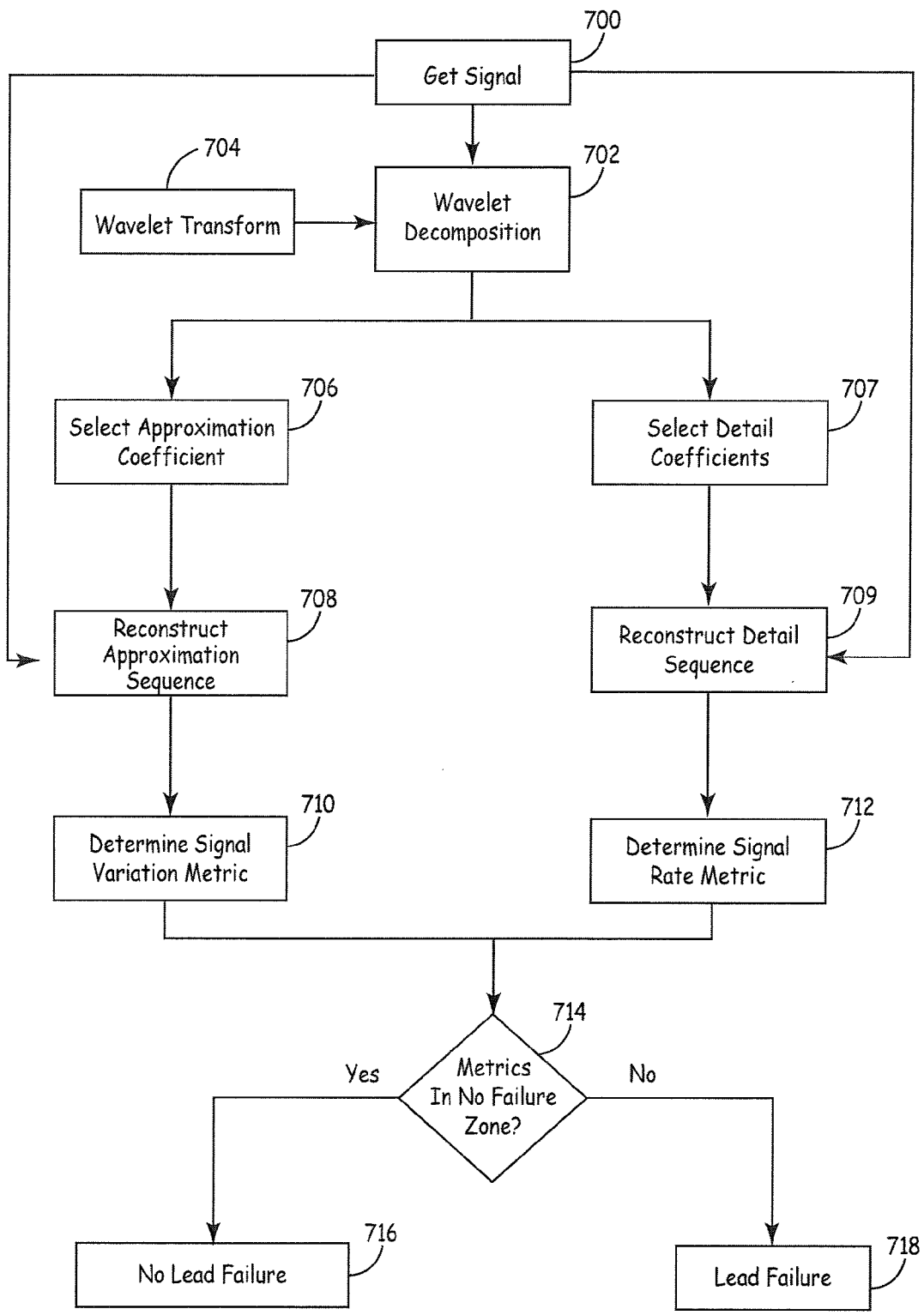
FIG. 8 is a flowchart of a method for detecting lead failure according to an embodiment of the present invention.

FIG. 8 is a flowchart of a method for detecting lead failure according to an embodiment of the present invention. As illustrated in FIG. 8, according to another embodiment of the invention, an EGM signal associated with cardiac signals sensed by the device is acquired, Block 700, so that a wavelet decomposition is performed, Block 702, on the obtained signal using a wavelet transform, Block 704, such as a Haar wavelet for example. According to an embodiment of the invention, the wavelet decomposition utilized in Block 702 is performed to 4 levels, implying a scale of $2^4$ as the course scale. Once the wavelet decomposition has been performed, the device selects the approximation coefficients, Block 706, previously obtained from the determined wavelet decomposition of Block 702. For example, according to an embodiment of the present invention, the device selects the approximation coefficient at the most course scale, i.e., $S=2^4$.

The approximation sequence, or signal is then re-constructed, Block 708, using the initially detected EGM signal, Block 700, obtained prior to the wavelet decomposition, Block 702, and the selected approximation coefficient, Block 706. Once the approximation sequence has been reconstructed in Block 708, the device determines a signal variation metric, Block 710, described below, based on the reconstructed signal, Block 708.

Once the wavelet decomposition has been performed, Block 702, the device also selects detail coefficients, Block 707, obtained previously from the determined wavelet decomposition of Block 706. For example, according to an embodiment of the invention, the device selects the detail coefficients at the finest scale, i.e., S=2, and the detail coefficient of the next finest scale, i.e., S=$2^2$.

The detail sequence, or signal, is then reconstructed, Block 709, using the initially detected EGM signal, Block 700, obtained prior to the wavelet decomposition, Block 702, and the selected detail coefficients, Block 707. For example, the device sets the reconstructed detail sequence, Block 709, as the sum of the sequences reconstructed from each of the two detail coefficients at the finest scale (S=2) and the next finest scale (S=$2^2$). Once the detail sequence has been reconstructed in Block 709, the device determines a signal rate metric, Block 712, described below, based on the reconstructed detail sequence, Block 709.

Once both the signal variation metric and the signal rate metric are determined, the device determines whether both the signal variation metric and the signal rate metric are within a no lead failure zone, Block 714, described below. If both the signal variation metric and the signal rate metric are within the no lead failure zone, Yes in Block 714, a lead failure is not detected, Block 716, and the detection and therapy delivery process resumes as normal. If one or both of the signal variation metric and the signal rate metric are outside the no lead failure zone, No in Block 714, a lead failure is detected, Block 718, and VTNF detection is withheld, thereby enhancing specificity. In addition, repeated lead failure detections may trigger a patient alert.

As described above, the signal variation metric and the signal rate metric are chosen in such a way as to maximize both the sensitivity and the specificity of the device in identifying a lead failure. For example, the inventors have discovered that both specificity and sensitivity are maximized by using the combination of a mean rectified amplitude MRA associated with the reconstructed signal of Block 708 as the signal variation metric in Block 710, and a mean absolute difference $MAD_{rr}$ between RR intervals associated with the reconstructed detail sequence obtained in Block 709 as the signal rate metric of Block 712.

Therefore, during the determination of the signal variation metric of Block 710, the device determines the generated sample amplitudes of the reconstructed signal of Block 708 over a predetermined window, such as a three second window for example, so that if the device generates the amplitude samples at a rate of 256 samples per second, the sampling results in 768 total amplitude samples being generated. The device then determines the mean rectified amplitude MRA associated with the three second window by dividing the sum of the absolute values of each of the amplitude samples by the number of samples, and sets the signal variation metric, Block 710, equal to the determined mean rectified amplitude MRA. Similarly, in order to determine the signal rate metric of Block 712, the device first determines an overall mean of a predetermined number of RR intervals from the reconstructed detail sequence, Block 709, determines the mean absolute difference $MAD_{rr}$ between the RR intervals by dividing the sum of the absolute differences between each RR interval and the overall mean by the number of samples, and sets the signal rate metric equal to the determined mean absolute difference $MAD_{rr}$.

According to another embodiment of the invention, the signal rate characteristic is determined based on the determined mean absolute difference $MAD_{rr}$, as described above in reference to FIG. 8. However, rather than utilizing the mean rectified amplitude MRA for the signal variation metric, the device determines an amplitude dispersion $DISP_A$ of the sample amplitudes for the three second window of the reconstructed approximation sequence by determining a difference between a maximum amplitude of the sample amplitudes and a minimum amplitude of the samples amplitudes, and sets the signal variation metric equal to the determined amplitude dispersion $DISP_A$. Therefore, both specificity and sensitivity are maximized by using the combination of an amplitude dispersion $DISP_A$ associated with the reconstructed signal of Block 408 as the signal variation metric, and a mean absolute difference $MAD_{rr}$ between RR intervals associated with the reconstructed detail sequence obtained in Block 709 as the signal rate metric.

Figure 9:
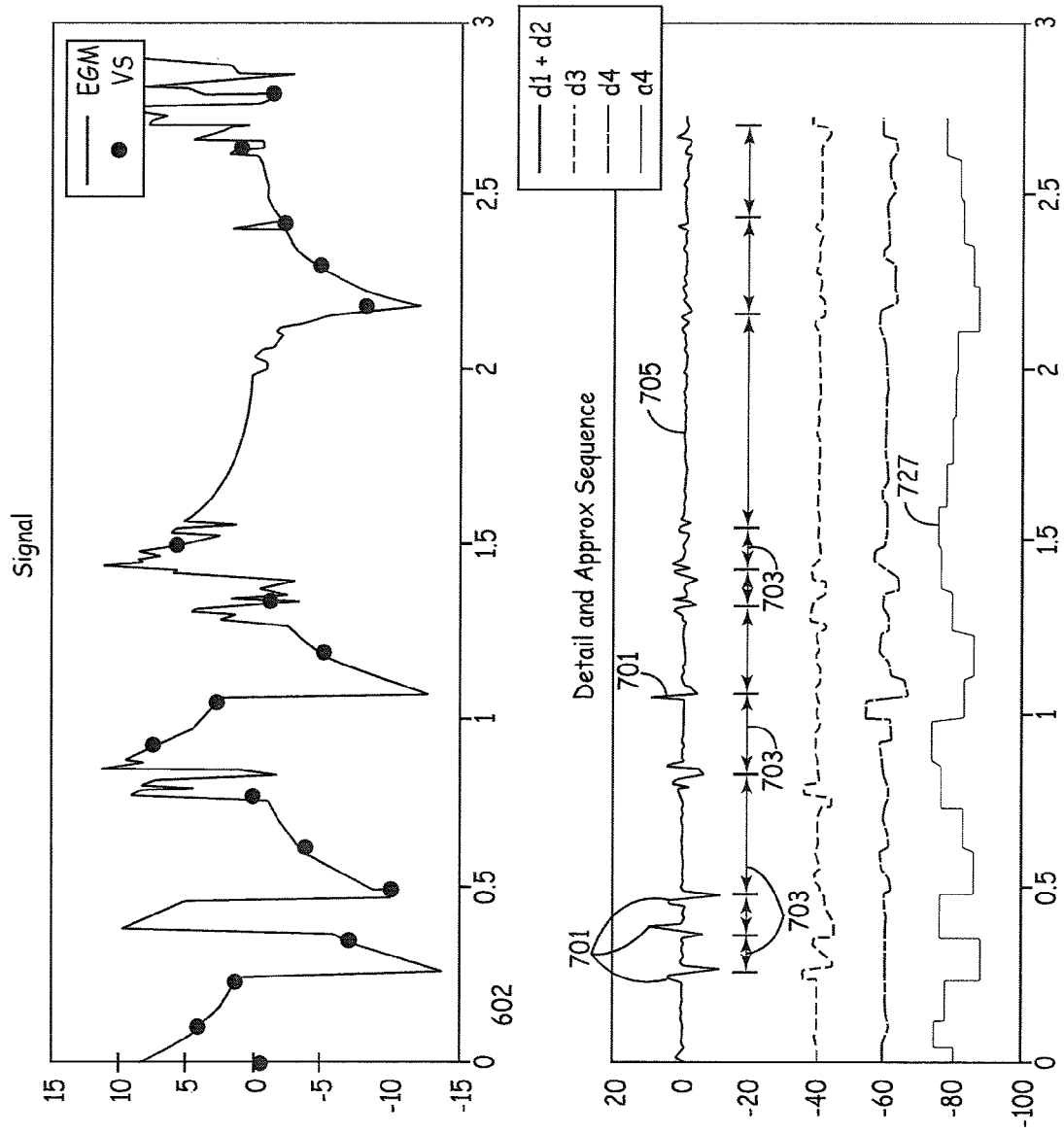
FIGS. 9 and 10 are graphical representations of detection of a lead failure according to an embodiment of the present invention.
Figure 10:
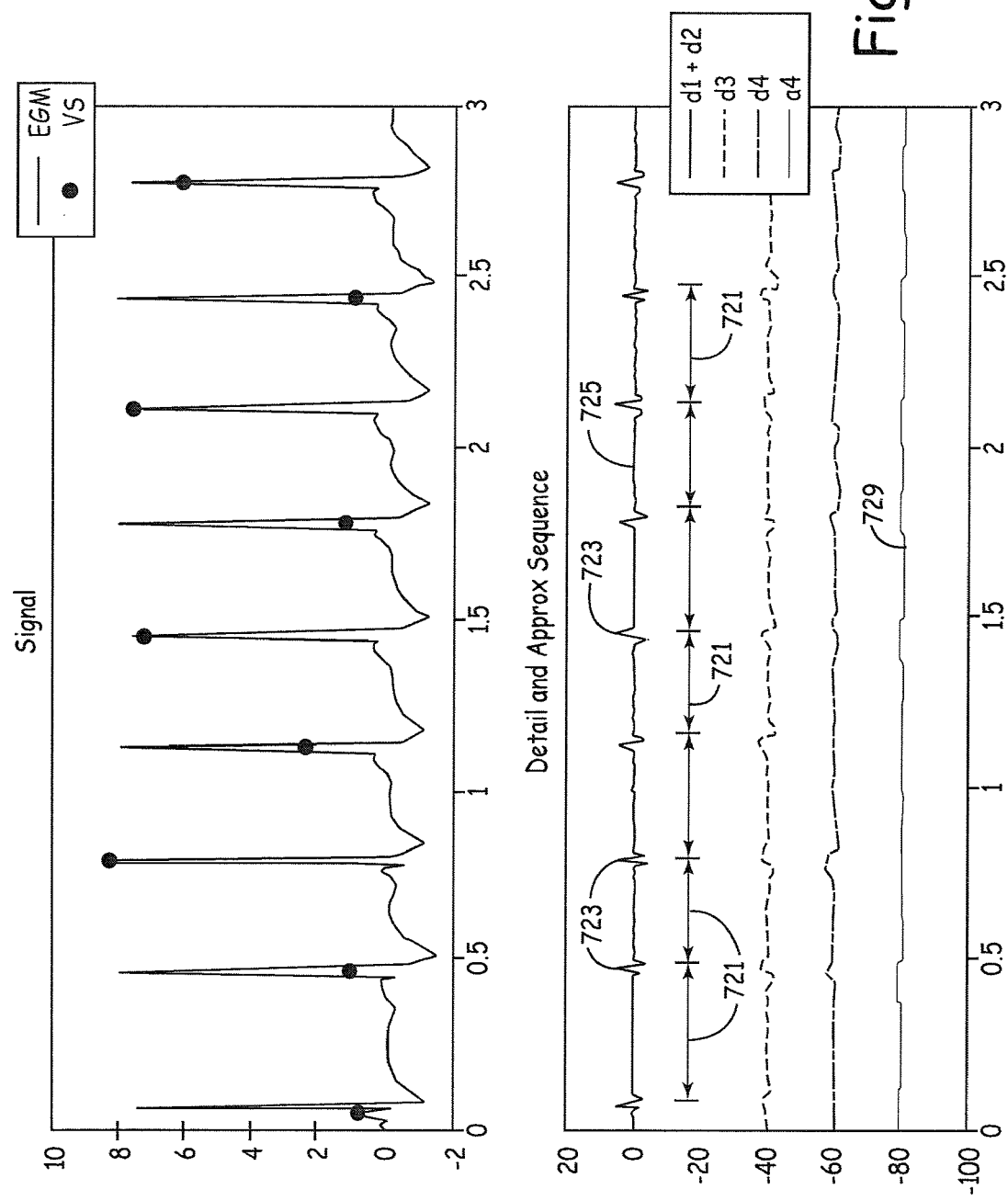

FIGS. 9 and 10 are graphical representations of detection of a lead failure according to an embodiment of the present invention. FIGS. 9 and 10 are exemplary illustrations of an appropriately detected lead failure and VF event. As illustrated in FIGS. 9 and 10, it can be deduced that the mean absolute difference between RR-intervals 703 associated with adjacent signal waves (i.e., R-waves) 701 of a detail sequence 705 associated with the sum of the detail sequence at the finest scale, S=2, and the detail sequence of the next finest scale, S=$2^2$ to generate the reconstructed detail sequence from Block 709 during a lead failure is greater than the mean absolute difference between RR-intervals 721 associated with adjacent R-waves 723 of a detail sequence 725 associated with the sum of the detail sequence at the finest scale, S=2, and the detail sequence of the next finest scale, S=$2^2$ to generate the reconstructed detail sequence from Block 709 resulting when there is VF with no lead failure. In addition, both a mean rectified amplitude associated with an approximation sequence at the most course scale 727 during lead failure is greater compared to an approximation sequence at the most course scale 729 when there is VF with no lead failure, and the amplitude dispersion associated with an approximation sequence at the most course scale 727 during lead failure is greater compared to the amplitude dispersion associated with an approximation sequence at the most course scale 729 when there is no lead failure.

Therefore, according to an embodiment of the invention of FIG. 8, the no lead failure zone 620 of FIG. 7 is defined based on the relationship between a predetermined mean rectified amplitude MRA threshold associated with the reconstructed approximation sequence of Block 708 and a mean absolute difference $MAD_{rr}$ threshold associated with the reconstructed detail sequence of Block 709 that is derived from one or more detail coefficients. According to the embodiment of FIG. 8, similar to the embodiment of FIG. 4, the MRA amplitude threshold is set as 4.7 and the $MAD_{rr}$ threshold is set as 52.5 ms. Similarly, according to another embodiment, the no lead failure zone 620 is defined based on the relationship between a predetermined amplitude dispersion $DISP_A$ threshold associated with the reconstructed signal of Block 408 and a mean absolute difference $MAD_{rr}$ threshold associated with the reconstructed detail sequence of Block 709 that is derived from one or more detail coefficients. In particular, for example, the no lead failure zone 620 is defined by a first boundary 622 associated with the amplitude dispersion $DISP_A$ threshold and a second boundary 624 associated with the mean absolute difference $MAD_{rr}$ threshold. According to an embodiment of the present invention, the dispersion $DISP_A$ threshold is set as 7 and the $MAD_{rr}$ threshold is set as 70 ms.

In this way, the signal variation metric and the signal rate metric are determined to be within the no lead failure zone 620 and therefore lead failure is not detected if both the mean rectified amplitude is less than the first boundary 622, i.e., the MRA threshold in one embodiment or the dispersion $DISP_A$ threshold in another embodiment, and the mean of the absolute differences is less than the second boundary, i.e., the $MAD_{rr}$ threshold.

As can be seen from the exemplary embodiments of FIGS. 4 and 8, the invention determines a lead failure using either a signal variation metric determined from a reconstructed approximation sequence resulting from wavelet decomposition combined with a mean absolute difference associated with RR intervals obtained either from the EGM signal or from the reconstructed detail sequence resulting from the wavelet decomposition. However, other discriminators may be utilized to determine lead failure according to the present invention. For example, according to another embodiment of the invention, the determination of lead failure is made using a metric based solely on one of a mean rectified amplitude, a mean amplitude difference, and an amplitude dispersion associated with the reconstructed approximation sequence of the wavelet decomposition, using the methods described above. As exemplary thresholds, the metric is determined to be in the no lead failure zone and therefore no lead failure is determined, if the mean rectified amplitude is less than 0.9, if the mean amplitude difference is less than 1, and if the amplitude dispersion is less than 5.9.

In addition, according to another embodiment of the invention, the determination of lead failure is made using a metric based solely on one of a mean interval difference and an interval dispersion associated with RR intervals from either the EGM signal or RR intervals from a reconstructed detail sequence of the wavelet decomposition. As exemplary thresholds, the metric is determined to be in the no lead failure zone and therefore no lead failure is determined, if the mean amplitude difference is less than 54.5 ms, and if the amplitude dispersion is less than 249.9 ms.

In currently known implantable cardiac devices, detection of a cardiac event is performed by keeping track of the number of RR intervals falling within a fibrillation detect interval (FDI) or tachy detect interval (TDI). According to an embodiment of the present invention, as RR intervals are acquired and whenever the NID is reached (eg. 12/16 or 18/24 within the TDI or FDI), then the prior 3-sec intracardiac EGM leading up to the time when the NID is met is processed according to the current embodiment to determine if there's lead failure. If lead failure is detected then VT/VF detection is withheld, otherwise detection process resumes as is currently defined.

While a particular embodiment of the present invention has been shown and described, modifications may be made. It is therefore intended in the appended claims to cover all such changes and modifications, which fall within the true spirit and scope of the invention.

We Claim:

1. A medical device, comprising:
    means for sensing cardiac signals to identify a predetermined cardiac event;
    a cardiac lead, the means for sensing cardiac signals being positioned, at least in part, with respect to the cardiac lead;
    means for applying a wavelet function to the sensed cardiac signals to generate a wavelet transform from the sensed cardiac signals using dyadic wavelet decomposition;
    means for generating a first wavelet representation from the wavelet transform, the first wavelet representation being responsive to highpass frequency content of the sensed cardiac signals;
    means for generating a second wavelet representation from the wavelet transform, the second wavelet representation being responsive to lowpass frequency content of the sensed cardiac signals;
    means for determining a no lead failure zone in response to the first wavelet representation and the second wavelet representation; and
    means for distinguishing the cardiac event from a lead failure of the cardiac lead in response to the determined no lead failure zone.

2. The device of claim 1, wherein the wavelet transform is a Haar wavelet transform, the first wavelet representation corresponds to a detail sequence, and the second wavelet representation corresponds to an approximation sequence.

3. The device of claim 1, wherein the wavelet transform is a Haar wavelet transform and the sensed cardiac signals are decomposed at a plurality of scales, the device further comprising:
    means for determining approximation coefficients and detail coefficients in response to the plurality of scales;
    means for reconstructing the second wavelet representation using predetermined approximation coefficients of the determined approximation coefficients; and
    means for reconstructing the first wavelet representation using predetermined detail coefficients of the determined detail coefficients, wherein the no lead failure zone is defined by a first boundary associated with the reconstructed first wavelet representation and a second boundary associated with the reconstructed second wavelet representation.

4. The device of claim 3, wherein the first boundary is determined in response to one of a mean absolute difference and a dispersion of RR intervals of the reconstructed first wavelet representation and the second boundary is determined in response to one of a mean rectified amplitude, a mean absolute difference, and a dispersion of the reconstructed second wavelet representation.

5. The device of claim 3, wherein the predetermined approximation coefficients correspond to a coarsest scale of the plurality of scales and the detail coefficients correspond to a finest scale of the plurality of scales.

6. The device of claim 5, wherein the approximation coefficients are determined at a fourth scale of the plurality of scales and the detail coefficients are determined at a first scale of the plurality of scales.

7. The device of claim 3, wherein the detail coefficients are determined at a first scale of the plurality of scales to form a first detail sequence and a second scale of the plurality of scales to form a second detail sequence, and wherein the first wavelet representation is reconstructed in response to a sum of the first detail sequence and the second detail sequence.

8. A medical device, comprising:
    means for sensing cardiac signals;
    a cardiac lead, the means for sensing cardiac signals being positioned with respect to the cardiac lead;
    means for decomposing the sensed cardiac signals using a wavelet function to form a corresponding wavelet transform using dyadic wavelet decomposition;
    means for generating a wavelet representation from the wavelet transform, the wavelet representation being responsive to lowpass frequency content of the sensed cardiac signals;
    means for determining RR intervals associated with the sensed cardiac signals;
    means for determining a no lead failure zone in response to the wavelet representation and the determined RR intervals; and means for distinguishing the cardiac event from a lead failure of the cardiac lead in response to the determined no lead failure zone.

9. The device of claim 8, wherein the wavelet transform is a Haar wavelet transform and the wavelet representation corresponds to an approximation sequence.

10. The device of claim 8, wherein the wavelet transform is a Haar wavelet transform and the sensed cardiac signals are decomposed at a plurality of scales, the device further comprising:
means for determining approximation coefficients in response to the plurality of scales; and
means for reconstructing the wavelet representation using predetermined approximation coefficients of the determined approximation coefficients, wherein the no lead failure zone is defined by a first boundary associated with the reconstructed wavelet representation and a second boundary associated with the determined RR intervals.

11. The device of claim 10, wherein the first boundary is determined in response to one of a mean rectified amplitude, a mean absolute difference, and a dispersion of the reconstructed wavelet representation and the second boundary is determined in response to one of a mean absolute difference and a dispersion of the determined RR intervals.

12. The device of claim 10, wherein the predetermined approximation coefficients correspond to a coarsest scale of the plurality of scales.

13. A medical device for sensing a cardiac signal of a patient, comprising:
a cardiac lead;
an electrode positioned with respect to the cardiac lead and configured to sense the cardiac signal;
a processor operatively coupled to the electrode and configured to:
applying a dyadic wavelet function to the cardiac signal to obtain a wavelet transform comprised of a plurality of wavelet values;
generate a low frequency wavelet representation from a plurality of lowpass wavelet values of the plurality of wavelet values of the wavelet transform;
generate a high frequency wavelet representation from a plurality of highpass wavelet values of the plurality of wavelet values of the wavelet transform;
determine a no lead failure zone based, at least in part, on the low frequency wavelet representation and the high frequency representation; and
distinguish a cardiac event from a failure of the cardiac lead based, at least in part, on the no lead failure zone.

14. The medical device of claim 13, further comprising a user interface operatively coupled to the processor and configured to display an indication of the failure of the cardiac lead to a user.

15. The medical device of claim 13, further comprising a therapy module operatively coupled to the processor and the electrode and configured to generate a predetermined therapeutic output; and
wherein the electrode is configured to deliver the therapeutic output to the patient;
wherein the predetermined therapeutic output is adjusted based, at least in part, on the failure of the cardiac lead.

16. The medical device of claim 13 wherein the processor is configured to apply the wavelet function to the cardiac signal to obtain the wavelet transform by being configured to:
apply a wavelet function to the signal function to obtain a subset of the plurality of highpass wavelet values and a subset of the plurality of lowpass wavelet values; then
apply the wavelet function to an immediately preceding subset of the plurality of lowpass wavelet values to obtain a subsequent subset of the plurality of highpass wavelet values and a subsequent subset of the plurality of lowpass wavelet values; then
repeat at least once the applying the wavelet function to an immediately preceding subset of the plurality of lowpass wavelet values.

17. The medical device of claim 16 wherein the plurality of highpass wavelet values is at least one subset of the plurality of highpass wavelet values and the plurality of lowpass wavelet values is at least one subset of the plurality of lowpass wavelet values.

18. The medical device of claim 17 wherein the at least one subset of the plurality of highpass wavelet values is a subset of the plurality of highpass wavelet values obtained first in sequence and the at least one subset of the plurality of lowpass wavelet values is a subset of the plurality of lowpass wavelet values obtained last in sequence.

19. The medical device of claim 18 wherein the at least one subset of the plurality of lowpass wavelet values is a fourth subset of lowpass wavelet values obtained in sequence.

20. The medical device of claim 17 wherein the plurality of highpass wavelet values is an aggregate of at least some subsets of the plurality of highpass wavelet values.

21. The medical device of claim 20 wherein the plurality of highpass wavelet values is an aggregate of a subset of the plurality of highpass wavelet values obtained first in sequence and a subset of the plurality of highpass wavelet values obtained second in sequence.

* * * * *